(12) United States Patent
Chu et al.

(10) Patent No.: US 8,969,547 B2
(45) Date of Patent: Mar. 3, 2015

(54) METHOD FOR PREPARING FLUTICASONE FUROATE

(71) Applicants: Zhejiang Tiantai Aurisco Pharmaceutical Co. Ltd., Tiantai, Zhejiang Province (CN); Shanghai Aurisco Industry Co., Ltd., Shanghai (CN)

(72) Inventors: Dingjun Chu, Tiantai (CN); Haijie Ji, Tiantai (CN); Xiangxian Hong, Tiantai (CN)

(73) Assignees: Zhejiang Tiantai Aurisco Pharmaceuticals Co. Ltd., Tiantai, Zhejiang Province (CN); Shanghai Aurisco Industry Co., Ltd., Shanghai (CN)

( * ) Notice: Subject to any disclaimer, the term of this patent is extended or adjusted under 35 U.S.C. 154(b) by 78 days.

(21) Appl. No.: 13/913,378

(22) Filed: Jun. 7, 2013

(65) Prior Publication Data

US 2013/0274461 A1    Oct. 17, 2013

Related U.S. Application Data

(63) Continuation of application No. PCT/CN2011/001146, filed on Jul. 11, 2011.

(30) Foreign Application Priority Data

Dec. 14, 2010    (CN) .......................... 2010 1 0588166

(51) Int. Cl.
| | | |
|---|---|---|
| *C07J 17/00* | (2006.01) | |
| *C07J 31/00* | (2006.01) | |
| *C07J 71/00* | (2006.01) | |

(52) U.S. Cl.
CPC ................ *C07J 31/006* (2013.01); *C07J 17/00* (2013.01); *C07J 31/00* (2013.01); *C07J 71/00* (2013.01)
USPC ........................................................ 540/114

(58) Field of Classification Search
USPC ........................................................ 540/114
See application file for complete search history.

(56) References Cited

U.S. PATENT DOCUMENTS 4,335,121 A    6/1982    Phillipps et al.

FOREIGN PATENT DOCUMENTS

| GB | 2088877 B | 7/1984 |
|---|---|---|
| WO | WO 02/12265 A1 | 2/2002 |
| WO | WO 03/066036 A1 | 8/2003 |
| WO | WO 03/066655 A1 | 8/2003 |
| WO | WO 2007/144363 A2 | 12/2007 |

*Primary Examiner* — Brenda Coleman
(74) *Attorney, Agent, or Firm* — Manni Li; Mei & Mark LLP

(57) ABSTRACT

Method for preparing fluticasone furoate (6α,9α-difluoro-11β-hydroxy-16α-methyl-17α-[(2-furoyl)oxy]-3-oxo-androsta-1,4-diene-17β-carbothioic acid S-fluoromethyl ester) by directly subjecting a compound of Formula III and a complex of a fluoromethylating reagent in presence of an organic base to a replacement reaction to obtain the target compound. Generation of impurities in a process via Compound IV is avoided; the method is simple with mild reaction conditions, suitable for industrial production, and yields products with purity of 98% by HPLC.

17 Claims, No Drawings

METHOD FOR PREPARING FLUTICASONE FUROATE

CROSS-REFERENCE AND RELATED APPLICATIONS

The subject application is a continuation of PCT international application PCT/CN2011/001146 filed on Jul. 11, 2011, which in turn claims priority on Chinese patent application No. CN 201010588166.1 filed on Dec. 14, 2010. The contents and subject matter of the PCT and Chinese priority applications are incorporated herein by reference.

FIELD OF THE INVENTION

The present invention relates to method for synthesizing pharmaceutical compounds, particularly, method for preparing fluticasone derivatives.

BACKGROUND OF THE INVENTION

Glucocorticoids have anti-inflammatory properties and are widely used for the treatment of inflammatory disorders or diseases such as asthma and rhinitis. For examples, U.S. Pat. No. 4,335,121 discloses fluticasone propionate and derivatives thereof; WO 2002/012265 discloses a fluticasone derivative, fluticasone furoate, represented by formula I:

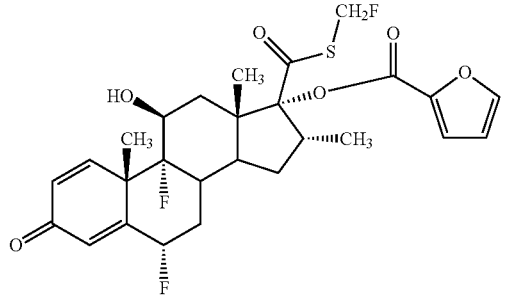

The chemical name of Compound I is 6α,9α-difluoro-11β-hydroxy-16α-methyl-17α-[(2-furoyl)oxy]-3-oxo-androsta-1,4-diene-17β-carbothioic acid S-fluoromethyl ester. The compound and fluticasone propionate were both developed by GlaxoSmitheKline. Based on the current studies, Compound I may be used for treating skin diseases, such as eczema, psoriasis, allergic dermatitis, neurodermatitis, pruritis, and hypersensitivity reactions; inflammatory conditions of the nose, throat, or lungs, such as asthma (including allergen-induced asthmatic reactions), rhinitis (including hayfever), nasal polyps, chronic obstructive pulmonary disease, interstitial lung disease, and fibrosis; inflammatory bowel conditions, such as ulcerative colitis and Crohn's disease; and auto-immune diseases, such as rheumatoid arthritis. The compound may also have use in the treatment of conjunctiva and conjunctivitis.

Methods for preparing the Compound of formula I are known. WO2002/012265 provides the following methods:

Method 1 provides that Compound IV reacts with bromofluoromethane or fluorochloromethane to obtain the target Compound I as follows:

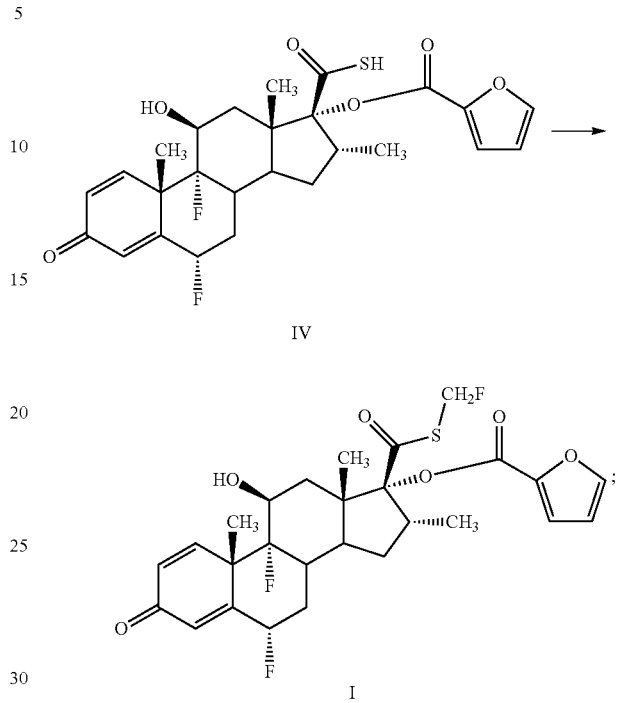

Method 2 provides that Compound V undergoes a 9-carbon fluoridating reaction to obtain the target Compound I as follows:

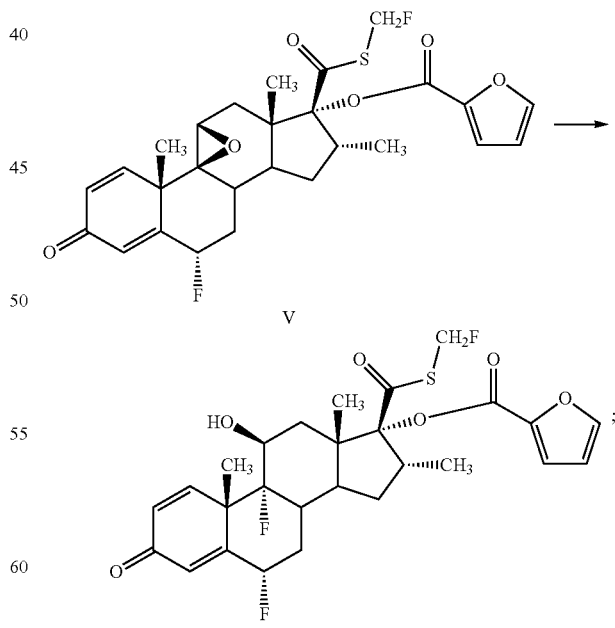

Method 3 provides that 11-carbonyl group of Compound VI is reduced to obtain the target Compound I:

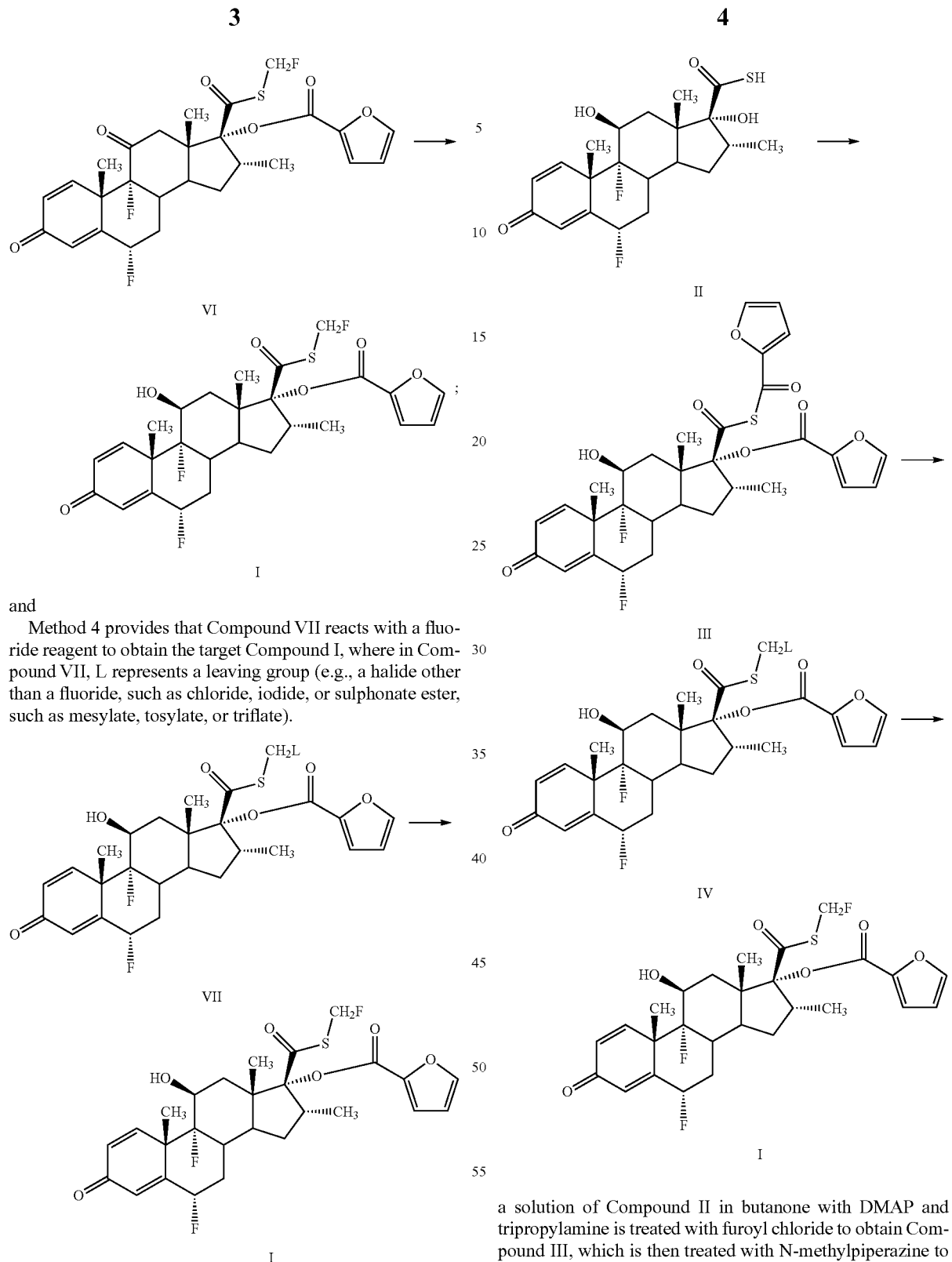

and

Method 4 provides that Compound VII reacts with a fluoride reagent to obtain the target Compound I, where in Compound VII, L represents a leaving group (e.g., a halide other than a fluoride, such as chloride, iodide, or sulphonate ester, such as mesylate, tosylate, or triflate).

In these methods, Method 1 is the only method that can be used for commercial production by reacting Compound IV with a fluoromethylating reagent to obtain the target Compound I.

Based on Method 1, WO 2007/144363 to GlaxoSmitheKline discloses the following reactions for making the Compound I:

a solution of Compound II in butanone with DMAP and tripropylamine is treated with furoyl chloride to obtain Compound III, which is then treated with N-methylpiperazine to de-fluoridize to obtain Compound IV. Compound IV is reacted with a fluoromethylating reagent to obtain the fluticasone furoate of Compound I. The method is performed in a homogeneous system, without isolating the Compounds III and IV, to obtain the final product of Compound I by a one-pot method.

These two methods are via the Compound IV, and reacting Compound IV with a fluoromethylating reagent to obtain Compound I. But Compound IV is unstable, hard to purify, thus the quality of Compound I is relatively low. Further, the preparation steps for Compound IV have disadvantages including more reaction steps, higher cost, more difficult to handle, and produces more industrial wastes.

DETAILED DESCRIPTION OF THE INVENTION

The present invention solves the above-mentioned problems by designing an easy, efficient, and economical method for preparing the fluticasone furoate of formula I, which is suitable for commercial production.

The present invention provides a method for preparing the fluticasone furoate of formula I (6α,9α-difluoro-11β-hydroxy-16α-methyl-17α-[(2-furoyl)oxy]-3-oxo-androsta-1, 4-diene-17β-carbothioic acid S-fluoromethyl ester).

The present invention includes the following steps:

(1) Forming an amine salt by Compound II (6α,9α-difluoro-11β-hydroxy-16α-methyl-17α-hydroxy-3-oxo-androsta-1,4-diene-17β-carbothioic acid) and triethylamine in a solvent of a ketone, ester, or alkyl halide, and reacting with furoyl chloride at the temperature of −10° C. to 40° C. to obtain Compound III (6α,9α-difluoro-17-carboxylic furan-2-carboxylic thioanhydride-11β-hydroxy-16α-methyl-3-oxoandrosta-1,4-diene-17α-yl furoate);

(2) In a solvent of an alcohol, ketone, or amide, forming a complex of a fluoromethylating reagent and an organic base at the complex formation temperature of −10° C. to 30° C., and then, subjecting Compound III and the complex of the fluoromethylating reagent and the organic base to a replacement reaction between the fluoromethyl group of the complex and the furoyl group of the Compound III to obtain the target product of Compound I.

The chemical process is as follows:

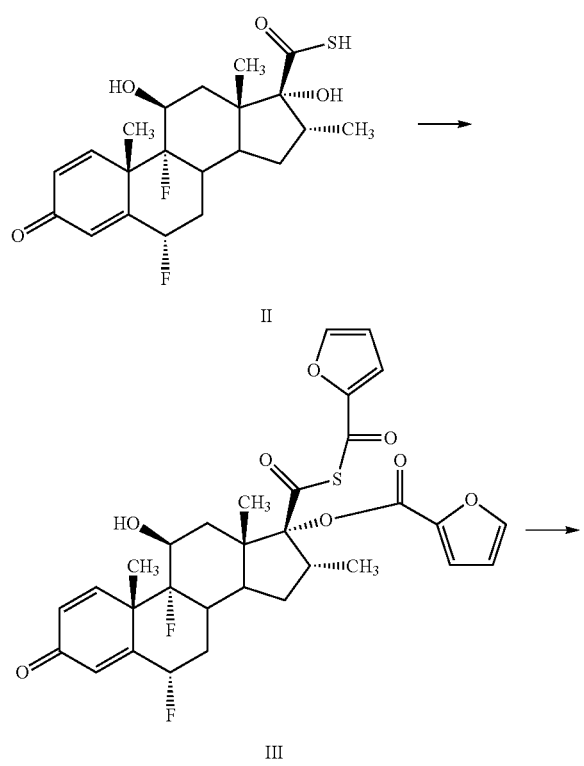

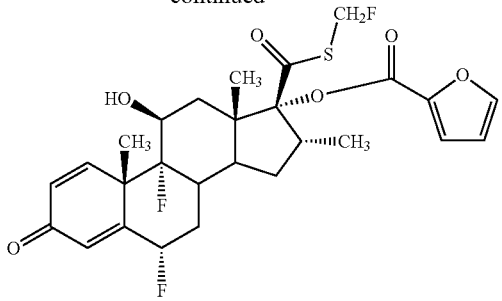

The characteristics of the present invention include:

(a) In the process of converting Compound II to Compound III, triethylamine is used as an acid-binding reagent, forming triethylamine salts by triethylamine and 17-carbothioic acid of Compound II, and reacting with furoyl chloride to obtain Compound III. The molar amount of furoyl chloride is 2 to 3 times of that of Compound II. The temperature is at −10° C. to 30° C., and preferably, −5° C. to 5° C. Suitable solvents include an ester, ketone, or alkyl halide, such as ethyl acetate, acetone, butanone, or dichloroethane.

(b) Compound III obtained from step (a) may be filtered and isolated to obtain a highly purified Compound III and then converted to Compound I by the replacement reaction. Alternatively, the compound is not isolated but directly reacts with the complex of the fluoromethylating reagent and the organic base to obtain Compound I.

(c) Compound III obtained from step (a) and the complex of the fluormethylating reagent and the organic base react in the replacement reaction between fluoromethyl and furoyl groups to obtain Compound I. The fluoromethylating reagent may be bromofluoromethane or chlorofluoromethane, and preferably, bromofluoromethane. The organic base may be 4-dimethylaminopyridine pyridine (DMAP), N-methyl piperazine, diethyl amine, pyridine, or α-methylpyridine, and preferably, 4-dimethylpyridine. The solvent may be N,N-dimethyl formamide (DMF), N,N-dimethyl acetamide (DMA), acetone, or butanone, and preferably, DMF or acetone, or a mixture of the above. The alcohol-type solvent, such as methanol or ethanol, may be added in excess, such as in the molar amount of 1 to 50 times more than that of Compound III, which benefits the reaction.

In the reaction of the present invention, the amount of bromofluoromethane used may be slightly in excess, for example, 1.2 equivalent weight of Compound III is reacted with 1 equivalent weight of DMAP to form the complex. The complex temperature is at −10° C.~30° C., preferably at 10° C.~20° C. Then, the isolated Compound III or a reaction mixture containing Compound III, undergoes the replacement reaction at the suitable temperature, e.g., −10° C.~30° C., and preferably 15° C.~25° C. After the reaction is completed, 0.5~10 times water or acid water, such as 0.1~2N diluted hydrochloric acid, is added and crystallized solids are formed and isolated, filtered, and dried to obtain Compound I with high quality.

In the present invention, Compound III directly reacts with the complex of the fluoromethylating reagent for the replacement reaction to obtain the target compound of formula I, thus, the process avoids the reaction route via Compound IV, simplifies the process, produces less impurities from preparing Compound IV, improves the product quality (higher than the purity at 97.4% as disclosed in WO 2007/144363), and is more suitable for industrial production.

Compound II in the present invention, 6α,9α-difluoro-11β-hydroxy-16α-methyl-17α-hydroxy-3-oxo-androsta-1,4-diene-17β-carbothioic acid, is prepared as the method in GB2088877B. DMF is used as solvent, Compound VIII, i.e., fluoromethasone acid reacts with carbonyldimidazole, and hydrogen sulphide gas is added in the reaction to obtain the target compound. The reaction is as follows:

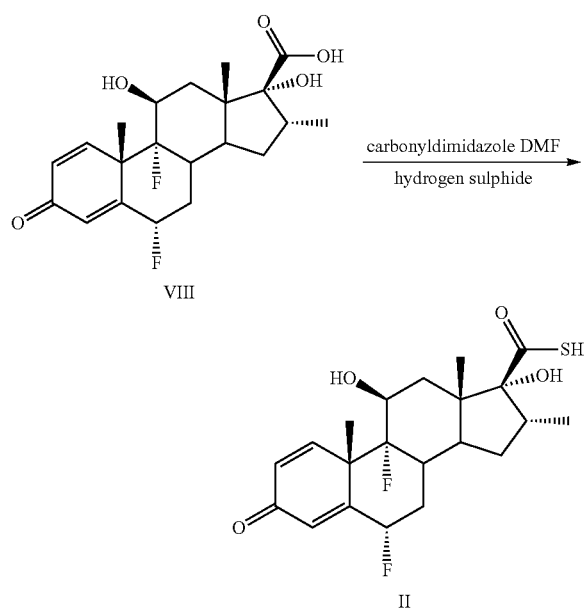

The present invention provides simplified operational procedures and mild reaction conditions, and product has high purity. The method of the present invention is suitable for large-scale industrial production.

The following examples are intended to illustrate the embodiments of the present invention and do not serve to limit the scope of the present invention.

Example 1

Preparation of 6α,9α-difluoro-11β-hydroxy-16α-methyl-17α-hydroxy-3-oxo-androsta-1,4-diene-17β-carbothioic acid (Formula II)

In the protection of the nitrogen gas atmosphere, a mixture of 100 g flumethasone acid, 1900 g DMF, and 95 g carbonyldimidazole are stirred at room temperature for 4 hours. Then, hydrogen sulphide gas is added, and the process is monitored using TLC until the reaction is complete. 4 L 2N hydrochloric acid and 2 Kg water are poured into the solution, stirring to crystallize solids, which are filtered and dried to obtain approximately 95 g Compound II at a purity of 97.5%.

Example 2

Preparation of 6α,9α-difluoro-17-carboxylic furan-2-carboxylic thioanhydride-11β-hydroxy-16α-methyl-3-oxoandrosta-1,4-diene-17α-yl furoate (formula III)

A mixture of 100 g and 0.242 mol of 6α,9α-difluoro-11β-hydroxy-16α-methyl-17α-hydroxy-3-oxo-androsta-1,4-diene-17β-carbothioic acid of formula II and 1260 g acetone is cooled to −5° C.~5° C. Then, 50 g and 0.494 mol of triethylamine is added. Thereafter, 66 g and 0.506 mol of furoyl chloride is added dropwise and reacted for 0.5 hour. Then, the product is filtered to obtain 140 g Compound III at a purity of 98.2%.

Example 3

Preparation of 6α,9α-difluoro-11β-hydroxy-16α-methyl-17α-[(2-furoyl)oxy]-3-oxo-androsta-1,4-diene-17β-carbothioic acid S-fluoromethyl ester (Formula I, fluticasone furoate)

A mixture of 500 g acetone, 25 g DMAP, and 18.6 g and 0.125 mol of bromofluoromethane are stirred for 3 hours at 5° C.~10° C. Then, 6α,9α-difluoro-11β-hydroxy-16α-methyl-17α-hydroxy-3-oxo-androsta-1,4-diene-17β-carbothioic acid obtained from Example 2, at the amount of 50 g and 0.083 mol, is added to react at 15° C.~25° C. The progress is monitored using TLC until the reaction is complete. The solution is added with water to crystallize the solid which is filtered, washed, and dried to obtain fluticasone furoate 44 g at a purity of 98.3% as determined by HPLC.

Example 4

Preparation of 6α,9α-difluoro-11β-hydroxy-16α-methyl-17α-[(2-furoyl)oxy]-3-oxo-androsta-1,4-diene-17β-carbothioic acid S-fluoromethyl ester (formula I, fluticasone furoate)

A mixture of 375 g DMF, 22 g DMAP, and 18.6 g and 0.125 mol of bromofluorormethane are cooled to 10° C.~20° C. and stirred for 2 hours. After that, 6α,9α-difluoro-17-carboxylic furan-2-carboxylic thioanhydride-11β-hydroxy-16α-methyl-3-oxoandrosta-1,4-diene-17α-yl furoate obtained from Example 2 at the amount of 50 g and 0.083 mol and 40 g methanol are added and reacted for 1 hour at 15° C.~25° C. Then, water is added to crystallize the solid, which is filtered, washed, and dried to obtain fluticasone furoate 43 g at a purity of 98.7% as determined by HPLC.

Example 5

Preparing 6α,9α-difluoro-11β-hydroxy-16α-methyl-17α-[(2-furoyl)oxy]-3-oxo-androsta-1,4-diene-17β-carbothioic acid S-fluoromethyl ester (formula I, fluticasone furoate), without isolating Compound III A mixture of 6α,9α-difluoro-11β-hydroxy-16α-methyl-17α-hydroxy-3-oxo-androsta-1,4-diene-17β-carbothioic acid in the amount of 50 g and 0.121 mol and 600 g acetone is cooled to −5° C.~5° C. Then, triethylamine in the amount of 24.5 g and 0.242 mol is added. Thereafter, furoyl chloride is added dropwise in the amount of 31.6 g and 0.242 mol and reacted for 1 hour to obtain a reaction mixture of Compound III which is put to standby for use.

A mixture of 150 g DMF, 30 g DMAP, and 24 g bromofluoromethane is cooled to 10° C.~20° C. and stirred for 1 hour. Then, the mixture of Compound III and 50 g methanol are added to react at 15° C.~25° C. for 1 hour. The diluted hydrochloric acid is then added to crystallize the solid, which is filtered, washed, and dried to obtain fluticasone furoate 71 g with a purity of 97.8% as determined by HPLC.

We claim:

1. A method for preparing fluticasone furoate, comprising
   reacting Compound II (6α,9α-difluoro-11β-hydroxy-16α-methyl-17α-hydroxy-3-oxo-androsta-1,4-diene-17β-carbothioic acid) and triethylamine in a first solvent to obtain an amine salt,
   reacting the amine salt with furoyl chloride to obtain Compound III (6α,9α-difluoro-17-carboxylic furan-2-carboxylic thioanhydride-11β-hydroxy-16α-methyl-3-oxoandrosta-1,4-diene-17α-yl furoate),
   reacting a fluoromethylating reagent and an organic base in a second solvent to form a complex, and
   adding the Compound III to the complex to have a replacement reaction between a fluoromethyl group of the complex and a furoyl group of the Compound III to obtain Compound I (6α,9α-difluoro-11β-hydroxy-16α-methyl-17α-[(2-furoyl)oxy]-3-oxo-androsta-1,4-diene-17β-carbothioic acid S-fluoromethyl ester).

2. The method for preparing fluticasone furoate of claim 1, wherein molar amount of the furoyl chloride is about 2 to 3 times of molar amount of the Compound II in reacting the amine salt and the furoyl chloride to obtain the Compound III.

3. The method for preparing fluticasone furoate of claim 1, wherein the first solvent is acetone, butanone, ethyl acetate, or dichloromethane.

4. The method for preparing fluticasone furoate of claim 1, wherein temperature for reacting the amine salt with the furoyl chloride to obtain the Compound III is in a range of from about −10° C. to about 30° C.

5. The method for preparing fluticasone furoate of claim 4, wherein the temperature for reacting the amine salt with the furoyl chloride to obtain the Compound III is in the range of from about −5° C. to about 5° C.

6. The method for preparing fluticasone furoate of claim 1, further comprising
   filtering and isolating the Compound III from reaction mixture before adding the Compound III to the complex to obtain the Compound I via the replacement reaction.

7. The method for preparing fluticasone furoate of claim 1, wherein the Compound III is directly added to the complex to obtain the Compound I via the replacement reaction without being isolated.

8. The method for preparing fluticasone furoate of claim 1, wherein about 1.2 equivalent weight of the fluoromethylating reagent and about 1 equivalent weight of the organic base are reacted to form the complex.

9. The method for preparing fluticasone furoate of claim 1, wherein temperature for reacting the fluoromethylating reagent and the organic base to form the complex is in a range of from about −10° C. to about 30° C.

10. The method for preparing fluticasone furoate of claim 9, wherein the temperature for reacting the fluoromethylating reagent and the organic base to form the complex is in a range of from about 10° C. to about 20° C.

11. The method for preparing fluticasone furoate of claim 1, wherein temperature for adding the Compound III to the complex, while stirring, to carry on the replacement reaction is in a range of about −10° C. to about 30° C.

12. The method for preparing fluticasone furoate of claim 11, wherein the temperature for adding the Compound III to the complex, while stirring, to carry one the replacement reaction is in a range of about 15° C. to about 25° C.

13. The method for preparing fluticasone furoate of claim 1, further comprising
   adding water or 0.1~2N diluted hydrochloric acid in an amount of about 0.5 to 10 times of that of the second solvent to reaction mixture after the replacement reaction to crystallize solids, and
   filtering and drying the crystallized solids to obtain Compound I.

14. The method for preparing fluticasone furoate of claim 1, wherein the second solvent is acetone, butanone, methanol, ethanol, N,N-dimethyl formamide, N,N-dimethyl acetamide, or a mixture thereof.

15. The method for preparing fluticasone furoate of claim 1, wherein the fluoromethylating reagent is bromofluoromethane or fluorochloromethane.

16. The method for preparing fluticasone furoate of claim 1, wherein the organic base is 4-dimethylaminopyridine (DMAP), N-methyl piperazine, diethyl amine, pyridine, or α-methyl pyridine.

17. The method for preparing fluticasone furoate of claim 1, wherein the Compound II (6α,9α-difluoro-11β-hydroxy-16α-methyl-17α-hydroxy-3-oxo-androsta-1,4-diene-17β-carbothioic acid) is prepared by reacting Compound VIII (flumethasone acid) with carbonyldimidazole in N,N-dimethyl formamide as a solvent in presence of hydrogen sulfide.

* * * * *